US007126687B2

(12) United States Patent
Hill et al.

(10) Patent No.: US 7,126,687 B2
(45) Date of Patent: Oct. 24, 2006

(54) METHOD AND INSTRUMENTATION FOR DETERMINING ABSORPTION AND MORPHOLOGY OF INDIVIDUAL AIRBORNE PARTICLES

(75) Inventors: Steven Clyde Hill, Silver Spring, MD (US); Ronald Gene Pinnick, Columbia, MD (US); Yong-Le Pan, Cheshire, CT (US); Kevin Bruce Aptowicz, New Haven, CT (US); Kristan P. Gurton, Ashton, MD (US); Richard Kounai Chang, Hamden, CT (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 357 days.

(21) Appl. No.: 10/465,289

(22) Filed: Jun. 19, 2003

(65) Prior Publication Data
US 2003/0223063 A1 Dec. 4, 2003

Related U.S. Application Data

(60) Provisional application No. 60/389,544, filed on Jun. 19, 2002.

(51) Int. Cl.
*G01N 21/53* (2006.01)

(52) U.S. Cl. .......................... 356/336; 356/338; 356/343
(58) Field of Classification Search .................. 356/73, 356/336, 338, 340, 341, 343
See application file for complete search history.

(56) References Cited

U.S. PATENT DOCUMENTS

| 4,523,841 | A | * | 6/1985 | Brunsting et al. ............ 356/73 |
| 5,681,752 | A | * | 10/1997 | Prather ....................... 436/173 |
| 5,701,012 | A | * | 12/1997 | Ho ............................ 250/461.2 |
| 5,895,922 | A | * | 4/1999 | Ho ............................ 250/492.1 |
| 5,999,250 | A | * | 12/1999 | Hairston et al. .............. 356/73 |

* cited by examiner

*Primary Examiner*—F. L. Evans
(74) *Attorney, Agent, or Firm*—A. David Spevack; Guy M. Miller; Stephen M. Bloor

(57) ABSTRACT

Characterizing individual airborne particles in real time according to their absorption of optical energy at one or more wavelengths. The instrument can measure the two-dimensional angular optical scattering (TAOS) and/or the one-dimensional angular optical scattering (ODAOS) at one or more wavelengths. When two wavelengths are used, one is chosen to be on an absorption peak, the other is off of the absorption peak (preferably in the absorption valley).

18 Claims, 4 Drawing Sheets

Figure 1:
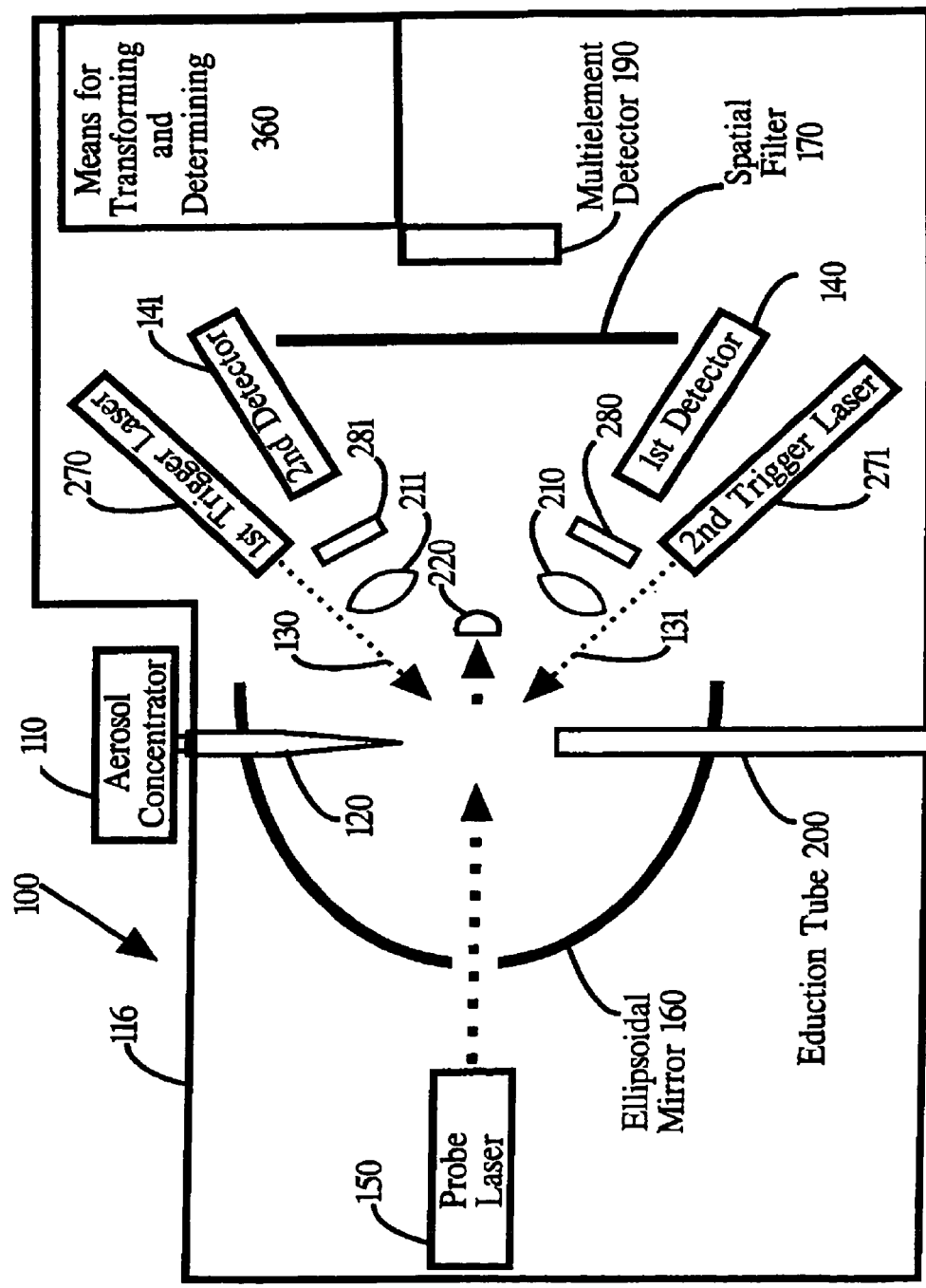

METHOD AND INSTRUMENTATION FOR DETERMINING ABSORPTION AND MORPHOLOGY OF INDIVIDUAL AIRBORNE PARTICLES

CROSS-REFERENCE TO RELATED APPLICATIONS

This Application is a Non-provisional application of U.S. Provisional Application No. 60/389,544; filed Jun. 19, 2002, benefit of the '544 application is claimed.

The present application is related to U.S. patent application Ser. No. 09/579,707 filed 25 May 2000 now U.S. Pat. No. 6,532,067 B1, which issued on 11 Mar. 2003, which in turn claims priority from Provisional U.S. Patent Application No. 60/147,794 filed on 9 Aug. 1999. The subject matter of the present application is also related to that in U.S. patent application Ser. No. 10/360,767, which retains the filing date 19 Jun. 2002 of the Provisional Patent Application Ser. No. 60/389,515, which is incorporated herein by reference. The '767 application is now U.S. Pat. No. 6,947,134, issued Sep. 20, 2005.

FEDERAL RESEARCH STATEMENT

The invention described herein may be manufactured and used by or for the United States Government for governmental purposes without the payment of any royalties thereon.

BACKGROUND OF INVENTION

Field of Invention

This invention pertains generally to rapid characterization of single airborne particles. The present invention describes method and instrumentation for providing information regarding absorptive properties and morphology (shape and internal structure) of individual airborne particles by measuring polarized light scattering over a large angular region at one or more wavelengths.

Aerosols are an important component of the earth's atmosphere. They limit atmospheric visibility; they affect cloud formation, the atmospheric propagation of laser beams, the performance of target acquisition systems, and the atmospheric radiation budget. Aerosols can affect the health of people, animals, and plants.

For example, bio-aerosols such as airborne microorganisms are found in workplaces and in homes. High concentrations may occur in or around buildings with defective air handling or air-conditioning systems, in houses with domestic animals, in manufacturing operations in which metal-working fluids are used, in meat-processing facilities, in dairy or other operations in which animals are confined, in sites of sludge application, in recycling or composting plants, and in sewage plants. Airborne microorganisms can cause diseases, and, along with other biological (e.g., dust mite allergens) and non-biological (e.g., diesel exhaust particles) aerosols can cause allergies and respiratory problems. Bioaerosols are also feared as biowarfare and terrorist agents.

Improved methods for measuring aerosols are needed, especially methods having rapid (real-time) response. In monitoring aerosols a rapid response may be necessary in situations where it would be impractical to continuously run a sampler/identifier. A real time monitor might suggest when to sample for specific harmful aerosols (especially bioaerosols). A monitor might be useful for measuring the dosage of medicines given through the human lung. Some studies of aerosol dynamics and reactions (evaporation, growth, agglomeration, mixing, etc.) require real-time monitoring capability. Finally, in searching for or studying intermittent sources of aerosols, a rapid response is advantageous.

Presently, most real time methods that measure aerosol in real time provide only particle size and concentration; little information about particle absorption and morphology is available.

Detecting absorption and morphology of particles is desirable for a variety of applications, such as in detecting fugitive aerosol emissions, differentiating between biological and non-biological aerosols (and classifying biological particles), or investigating aerosol drug-delivery systems.

Optical techniques are used extensively for aerosol measurement. They are non-intrusive, provide essentially real-time data, and are relatively easy to use. Techniques for measuring aerosol scattering using nephelometers, aerosol absorption using photo-acoustics, aerosol extinction using tranmissometry, and aerosol size and concentration using light scattering particle counters, have matured significantly over the last 25 years.

Of the techniques mentioned above, light scattering particle counters are one of the most widely used. They have been employed for determining estimates of the tropospheric and stratospheric aerosol burden, for monitoring concentrations of particles in clean rooms, and for detecting atmospheric aerosol pollutants. However, these instruments suffer from a critical limitation—they provide almost no information about particle absorption and morphology.

Light scattering particle counters are based on a single-particle detection approach, wherein particles entrained in air are rapidly drawn through an intense light beam, and light scattered by single particles is sensed and used to infer particle size. During the past thirty years, this approach has been expanded to measurement of one-dimensional and two-dimensional angular scattering of single aerosol particles. See, e.g., Wyatt, P. J., Schehrer, K. L., Phillips, S. D., Jackson, C., Chang, Y-J., Parker, R. G., Phillips, D. T., and Bottiger, J. R., (1988), *Aerosol Particle Analyzer*, Appl. Opt. 27, 217–221, incorporated herein by reference.

This approach has also been used to expand the measurement of intrinsic laser-induced fluorescence (LIF) of particles as well. See, e.g., Pinnick, R. G., Hill, S. C., Nachman, P., Pendleton, J. D., Fernandez, G. L., Mayo M. W., Bruno J. G., (1995), *Fluorescence Particle Counter for Detecting Airborne Bacteria and Other Biological Particles*, Aerosol. Sci. Tech. 23: 653–664, Hairston, P. P., Ho, J., Quant, F. R. (1997), *Design of an Instrument for Real-time Detection of Bioaerosols Using Simultaneous Measurement of Particle Aerodynamic Size and Intrinsic Fluorescence*, Aerosol. Sci. Tech. 28: 471–482, Hill, S. C., Pinnick, R. G., Niles, S., Pan, Y. L., Holler, S., Chang, R. K., Bottiger, J., Chen, B. T., Orr, C. S., Feather, G. (1999), *Real-time Measurement of Fluorescence Spectra from Single Airborne Biological Particles*, Field Anal. Chem. Tech., 3 (4–5): 221–239, and Pan, Y. L., Cobler, P., Rhodes, S., Potter, A. Chou, T., Holler, S., Chang, R. K., Pinnick, R. G. and Wolf, J-P. (2001), *High-speed High-sensitivity Aerosol Fluorescence Spectrum Detection Using a 32-anode Photomultiplier Tube Detector*, Rev. Sci. Instr. 72: 1831–1836, all of which are incorporated herein by reference.

The present invention is an improvement over that demonstrated by Gucker, F. T., Tuma, J., Lin, H-M., Huang, C-M., Ems, S. C., and Marshall, T. R. (1973), *Rapid measurement of light-scattering diagrams from single par-*

*ticles in an aerosol stream and determination of latex particle size*, Aerosol Sci. 4, 389–404., incorporated herein by reference. Gucker discloses a cw laser-based, single particle, flow-through, multiple-scattering instrument for aerosol measurement. Gucker measured scattering signals at polar angles 7 deg through 173 deg, using an ellipsoidal mirror and rotating aperture to collect and focus the scattered light onto a photomultiplier tube detector. By comparing measured angular scattering patterns to Mie theory, Gucker was able to precisely size polystyrene latex particles of known refractive index.

The present invention is also an improvement over of that demonstrated previously by the work of Gary C. Salzman in 1975. Salzman developed a cw laser-based, single-particle, flow-through, multiple-scattering angle cytometer for particles suspended in liquid. Salzman measured the forward scattering signals at 32 polar angles between 0.1 deg and 30 deg, using an array of 32 photodiodes, to discriminate between categories of cells.

The present invention is also an improvement over that demonstrated previously by Grams, G. W., Dascher, A. J., and Wyman, C. M. (1975), *Laser Polar Nephelometer for Airborne Measurements of Aerosol Optical Properties*, Optical Engineering, 14: 85–90, incorporated herein by reference. Grams discloses a cw laser-based, flow-through, multiple scattering angle polar nephelometer suitable for aircraft use. Grams used the polar nephelometer to measure the scattering of light by particles ranging from polar angles between 30 deg through 160 deg, and compared these measurements to model calculations for spherical particles to infer an average particle refractive index.

The present invention is also an improvement over that demonstrated previously by Bartholdi, M, Salzman, G. C., Hiebert, R. D., and Kerker, M. (1980), *Differential Light Scattering Photometer for Rapid Analysis of Single Particles in Flow*, Appl. Opt. 19, 1573–1581, incorporated herein by reference. Bartholdi discloses a cw laser-based, single-particle, flow-through, multiple-scattering angle cytometer for particles suspended in liquid. Bartholdi measured the scattering signals at 60 polar angles ranging from 2.5 deg through 177.5 deg (with each polar angle corresponding to a different azimuthal angle, and azimuthal angles spanning a range of 355 deg), using an ellipsoidal mirror to collect the scattered light from particles passing through one focal point of the mirror, and focusing the light onto a circular array of photodiode detectors placed near the second focal point of the mirror.

The present invention is also an improvement over that demonstrated previously by Bickel, W. S., Hashim, A. Y., and Bailey, W. M. (1982), *Masking of Information in Light Scattering Signals from Complex Scatterers*, Aerosol Sci. and Technol., 1; 329–335, incorporated herein by reference. Bickel discloses Mie theory calculations for non-absorbing and absorbing spheres to show that the polar angular scattering is sensitive to particle absorption.

The present invention is an improvement over that disclosed in Wyatt, U.S. Pat. No. 4,693,602 issued Sep. 15, 1987, incorporated herein by reference and Dick, W. D., McMurry, P. H., and Bottiger, J. R. (1994), *Size And Composition Dependent Response Of The DAWN-A Multiangle Single-Particle Optical Detector*, Aerosol Sci. and Technol., 20; 345–362, also incorporated herein by reference. Wyatt and Dick disclose a cw laser-based, single-particle, flow-through, multiple-scattering angle instrument for aerosol measurement. Wyatt measures the scattering signals at discrete polar angles 10 deg, 40 deg, 55 deg, 75 deg, 90 deg, 105 deg, 125 deg, 140 deg, and 170 deg, and for azimuthal angles every 45 deg, using a scattering cell consisting of two anodized aluminum hemispheres with 72 ports located on four great circles of the hemispheres at these angles, with single optical fibers coupled to each port, and with as many as 22 high-gain photomultiplier tubes coupled to the individual fibers for sensing the scattered light.

The present invention is also an improvement over Salzman, U.S. Pat. No. 4,884,886, issued 5 Dec. 1989 and incorporated herein by reference. Salzman discloses an apparatus, using a modulated polarized light source and detectors equipped with polarization analyzers, to make polar angular scattering measurements of up to 14 Mueller matrix elements on suspensions of biological particles.

The present invention is also an improvement over that demonstrated previously by Videen, G., and Bickel, W. S. (1992), *Light-Scattering Mueller Matrix for a Rough Fiber*, Appl. Opt. 31; 3488–3492, incorporated herein by reference. Videen discloses that the angular scattering characteristics of a 2.0 micrometer radius quartz fiber is modified by making the surface of the fiber rough. The rough surface creates higher-frequency, smaller-amplitude angular oscillations in scattering that mask the lower-frequency oscillations indicative of a perfect fiber.

The present invention is also an improvement over that demonstrated by Kaye, P. H. (1998), *Spatial Light-Scattering Analysis as a Means of Characterizing and Classifying Non-Spherical Particles*, Meas. Sci. Technol., 9, 141–149 and Kaye, P. H., Alexander-Buckley, K., Hirst. E., Saunders, S., and Clark, J. M. (1996), *A real-time monitoring system for airborne particle shape and size analysis*, J. Geophys. Res., 101, 19215–19221, both of which are incorporated herein by reference. Kaye discloses a cw-laser based, single-particle, flow-through, technique to measure the scattering of aerosol particles over polar angles from 27 deg through 140 deg. Kaye used an ellipsoidal mirror to collect and focus the scattered light onto three miniature photomultiplier tubes arranged symmetrically about the mirror axis such that each photomultiplier tube subtended complementary azimuthal angles. Kaye demonstrated the data could be used to differentiate spherical and nonspherical particles, and to classify nonspherical particles.

The present invention is also an improvement over that discloses by Kaye, P. H., Barton, J. E., Hirst. E., and Wang-Thomas, Z. (1997), *Neural-Network-lased Spatial Light-Scattering Instrument for Hazardous Airborne Fiber Detection*, Appl. Opt. 36, 6149–6156, incorporated herein by reference. Kaye discloses a cw-laser based, single-particle, flow-through, technique to measure the forward scattering of aerosol particles. Kaye measured the forward scattered light over polar angles 5 deg through 30 deg, and over azimuthal angles 0 deg through 360 deg, by focusing the light with a lens system onto an ICCD camera. The data are subsequently processed with an artificial neural network that has previously been trained to recognize patterns characteristic of asbestos fibers and other particles.

The present invention is also an improvement over that demonstrated previously by Holler, S., Pan, Y., Chang, R. K., Bottiger, J. R., Hill, S. C., and Hillis, D. B. (1998), *Two-Dimensional Angular Optical Scattering for the Characterization of Airborne Microparticles*, Opt. Lett. 23: 1489–1491, incorporated herein by reference. Holler discloses a single-particle, flow-through, multiple-scattering angle instrument employing a pulsed laser source. Holler measured the scattering signals of single aerosol particles over polar angles theta ranging over about 10 deg and azimuthal angles phi ranging over about 25 deg. Typical angular coverage for the Holler technique is a) 108 deg<theta<118 deg, 175 deg<phi<184 deg, and b) 87 deg <theta<94 deg, 14 deg<phi<41 deg. The Holler technique uses a lens (rather than a reflector or fiber bundles) for collection of scattered light and works best when the placement of the collection lens satisfies the Abbe-Sine condition. The Holler technique uses light scattered from a cw diode laser to trigger a diode pumped solid-state laser source (532 nm wavelength) and to trigger a gated ICCD detector.

The present invention is also an improvement over that demonstrated by Kaye, P. H., Barton, J. E., Hirst. E., and Clark, J. M. (2000), *Simultaneous Light Scattering and Intrinsic Fluorescence Measurement for the Classification of Airborne Particles*, Appl. Opt. 39: 373T8–3745, incorporated herein by reference. Kaye discloses a technique to measure simultaneously the ultraviolet laser-induced fluorescence and angular scattering of single aerosol particles as they traverse a cw laser beam. Kaye used an ellipsoidal mirror similar to that used in the present invention to collect the fluorescence, and a series of lenses to collect the elastic scattering over polar angles theta between 4 degrees and 30 degrees, and azimuthal angles phi between 0 degrees and 360 degrees. Kaye employed a multi-pixel (32 element) high-gain photodiode detector for measurement of the angular scattering.

The present invention is an advancement over the previous art for one or more of the following reasons, which will be described in more detail below: 1) The apparatus of the invention concentrates airborne particles (particularly micrometer-sized particles) by factors of several thousand using a combination of a virtual impactor and aerodynamic focusing nozzle; 2) these concentrated particles are focused into a stable aerosol jet where a cross-beam diode laser trigger subsystem detects the transit of single particles, and triggers a probe laser to fire and illuminate each particle in a small well-defined sample volume; 3) the probe laser is highly focused (and consequently has high-intensity), with beam waist of about the same cross section as both the sample volume and aerosol jet; 4) consequently the probe laser energy is used very efficiently; the probe laser fires only when particles are within the small sample volume, where particles are illuminated by the highly focused probe laser; 5) the sample volume is positioned to be at a focal point of a highly-reflective ellipsoidal mirror, which collects light scattered by the particle over a large solid angle (almost 2 $\pi$ steradians) in either the backward or forward scattering hemispheres; 6) scattered light is focused by the ellipsoidal mirror at the second focal point, where an aperture is positioned to reduce the passage of stray light; and 7) scattered light passing through the second focal point of the mirror is focused by a lens onto a gated ICCD detector, which is triggered to be open when the probe laser fires; the ICCD detector senses the light scattered by the particle over the large solid angle subtended by the ellipsoidal mirror, and with good angular resolution, as provided by the large number of pixels (typically 500×500) in the ICCD camera chip and with good angular resolution (typically better than 1 deg resolution in both polar and azimuthal angles). In addition, the LIF technique yields information only on fluorescent molecules found in microparticles. Consequently, these techniques have limited potential for providing information on particle absorption and morphology.

SUMMARY OF INVENTION

The present invention is a method and apparatus for characterizing the absorption and morphology of individual airborne particles rapidly by measurement of angular scattering of light at one or more wavelengths, or by measurement of thermal (as opposed to fluorescence) emission in addition to light scattering. An apparatus is provided which can measure two-dimensional angular scattering over a relatively large angular range (almost 2 $\pi$ steradians solid angle) and/or one-dimensional polar angular scattering, with high angular resolution and sensitivity, at one or more wavelengths, and at practical sample rates. When two wavelengths are used, one is chosen to be on an absorption peak, the other is off of the absorption peak (preferably in the absorption valley).

The use of two-dimensional angular scattering is especially useful for characterizing non-spherical or inhomogeneous particles. For homogeneous spheres, one-dimensional angular scattering at absorbing and non-absorbing wavelengths is adequate for determining the absorption by the particles.

The method is applicable to ultraviolet, visible, and infrared (IR) wavelengths. Infrared wavelengths are important because IR absorption spectra can have important spectral signatures (absorption bands) for molecules in aerosol particles, and because IR absorption can be particularly strong.

In the infrared, absorption at two wavelengths could be a good diagnostic tool. Aerosol particle absorption characteristics are of particular interest in the infrared, because the various molecules found in aerosol particles (ammonium sulphate, ammonium nitrate, sulfuric acid, terpenes, polycyclic aromatic hydrocarbons, heavy metal salts, quartz and clay minerals of soil origin, pollens and spores, etc) have distinct vibrational and rotational absorption bands in the 2–12 micrometer wavelength region. Thus, one of the two wavelengths can be chosen to be on an absorption band of a particular molecule and the other in an absorption valley.

Various other features, objects, and advantages of the present invention and the manner in which they are achieved will become apparent after reading the following detailed description, drawings, and claims.

BRIEF DESCRIPTION OF DRAWINGS

FIG. 1 is a schematic diagram illustrating the basic apparatus of the present invention;

FIG. 2 is a graph illustrating the Mie theory calculations that illustrate the method of the invention for determination of particle absorption characteristics in a simple case;

FIG. 3 is an ICCD image of angular scattering patterns obtained with the apparatus for a single 1 micrometer diameter polystyrene latex sphere (3*a*) and a 0.5 micrometer×1 micrometer *Bacillus subtilis* spore (3*b*) with scanning electron micrographs of the particles are shown in the inset; and FIG. 4 is an ICCD image of angular scattering patterns obtained with the apparatus for aggregate clusters of polystyrene latex and *Bacillus subtilis* spores. Micrographs of nominal 10 micron size clusters of 1 micrometer latex spheres, and 0.5 micrometer×1 micrometer *Bacillus subtilis* spores, are shown.

DETAILED DESCRIPTION

The apparatus and method of the present invention performs and uses the measurement of the angular scattering patterns (polarized or unpolarized) of individual airborne microparticles at one or more wavelengths. The angular scattering patterns depend on the size, refractive index (including the absorption), morphology, and orientation of the scattering particle (with respect to the direction and polarization of the illuminating laser). For a multi-component particle, the patterns depend also on the spatial distribution of refractive index within the particle. The information contained in the scattering patterns can be used to infer information about particle characteristics, particularly particle absorption and morphology.

FIG. 1 is a schematic diagram illustrating the basic apparatus 100 of the present invention. In the exemplar shown to illustrate the invention aerosol is drawn, at several hundred liters per minute, into an aerosol concentrator 110, a virtual impactor in the exemplar. Particle-laden air is then delivered, typically at about one liter per minute, to a focusing nozzle (nozzle) 120, which forms an aerosol jet. In this embodiment the nozzle 120 provides a second stage of aerosol concentration. The aerosol jet is directed through intersecting trigger laser beams (beams) 130 and 131 having different wavelengths, produced by a first 270 and second 271 trigger laser, respectively. Light scattered by single particles in the jet is filtered by first 280 and second 281 blocking filters. The first blocking filter 280 blocks the light from the second trigger laser 271, and the second blocking filter 281 blocks the light from the first trigger laser 270. In most embodiments the first 270 and second 271 trigger lasers are diode lasers. A portion of the light scattered by the single particles then passes through the first 280 and second 281 blocking filters and is sensed by a first 140 and second 141 photodetector. When the signals from both photodetectors (140 and 141) exceed (as determined using, for example, single channel analyzers, not shown) a preset threshold, the logic AND-gate (not shown) that receives the thresholded signals, then sends a the trigger pulse that signals for the probe laser 150 to fire and in some alternate embodiments signals to the multielement detector 190 to record data.

A probe laser 150, in the exemplar a frequency-doubled Nd:YAG, then illuminates the targeted aerosol particle at the focal point of an ellipsoidal mirror (mirror) 160. The particle scatters the probe laser 150 light in all directions; part of this scattered light is collected and re-focused by the ellipsoidal mirror 160. A spatial filter 170 positioned at the second focal point of ellipsoidal mirror 160 blocks stray light, but allows the light scattered by the targeted particle to pass. The light that passes through the spatial filter is then detected by the multielement detector 190.

The multielement detector 190 typically is an intensified charge-coupled device (ICCD) detector but may also be a charge-coupled device (CCD) detector, or may be a multi-anode photomultiplier tube (PMT) detector. Typically, the multielement detector also receives the trigger pulse from the AND circuitry, and records the angular scattering from the particle. In some embodiments a lens may be placed between the spatial filter 170 and the multielement detector 190 to colimate the light, and allow the detector 190 to be further from the spatial filter 170. In other embodiments, e.g., where a multielement detector 190 of a type that can be gated rapidly (e.g., an ICCD) is not used, a blocking filter may be placed in front of the mulitielement detector 190 to block the light from the trigger lasers.

In the exemplar shown the aerosol concentrator 110 uses a commercial Dycor model XMX virtual impactor concentrator, in which micrometer-sized particles entrained in air sampled at a few hundred liter/min are concentrated into an exit flow of about 1 liter/min. With a suitable concentrator 110, particles in the size range of 2–8 micrometers are concentrated in the exit flow with 30–40 percent efficiency.

This concentrated particle-laden air is then drawn, under negative pressure, typically at a rate of about 1 liter per minute, through a conically shaped nozzle 120. The preferred embodiment uses an 18-degree half-angle, 1 millimeter-diameter focusing nozzle, which is described in more detail in U.S. patent application Ser. No. 10/360,767, now U.S. Pat. No. 6,947,134, which is incorporated herein by reference. The concentrated particle-laden air is drawn into an airtight box 116, and eventually through an eduction tube 200 (exit port) aligned with focusing nozzle 120. In the exemplar the eduction tube 200 is located about 2 cm downstream from the nozzle 120. In the preferred embodiment the nozzle 120 aerodynamically focuses micrometer-sized particles because of their inertia, providing a further concentration enhancement in a focal spot about 5 millimeters below the nozzle 120, and the focal spot of the particles emanating from the nozzle in this region is about focusing nozzle 120 results in a particle sample rate that is size-dependent, but is of the order of a few liters per minute, which is a practical sample rate for monitoring atmospheric aerosol particles. In embodiments where no concentration enhancement is desired, or submicrometer particles are of primary interest, then the aerosol concentrator 110 may be eliminated. (In the exemplar described above using the Dycor XMX aerosol concentrator 110, neither this virtual impactor concentrator nor the aerodynamically focusing nozzle 120 works efficiently for submicrometer particles.) The region to which the particles are focused contains the "sample volume" described below, which is at one focus point of the ellipsoidal mirror, and is where a probe laser 150 is pulsed and directed so as to excite scattering by single particles as they pass through this sample volume.

Referring again to FIG. 1, two substantially perpendicular, intersecting, different wavelength, optically focused, trigger laser beams (first) 130 and (second) 131 are aligned to be within the aerosol focal spot. The intersection of the beams 130 and 131 from the first 270 and second 271 trigger lasers define a region slightly upstream (a few tens of micrometers in the preferred embodiment) from the sample region. When light from both the first 270 and second 271 trigger lasers is scattered by a particle, then signals from first 140 and second 141 photodetector are sensed. Light passing to the first 140 and second 141 photodetector may first pass through an appropriate first 210 or second 211 focusing lens respectively. When these signals from the first 140 and second 141 photodetectors both exceed some preset threshold then the probe laser 150 is triggered to fire and illuminate the particle in the sample volume. The sample volume is slightly downstream from the region of the crossed trigger laser beams, because of the finite time (approximately one microsecond in the exemplar) required for the probe laser 150 to fire.

The probe laser 150 illuminates the particle in the sample volume when it traverses one focal point of the ellipsoidal mirror 160, as depicted in the apparatus 100 shown in FIG. 1. Aerosol particles enter the scattering cell through the aerodynamically focusing nozzle 120. Particle trajectories from the nozzle 120 are sufficiently stable so that the aerosol jet remains collimated through the focal point of the mirror 160. The optically-focused probe laser enters the cell through a small aperature (6.35 mm diameter in the preferred embodiment) in the apex of the ellipsoidal mirror 160, and illuminates the particle in the direction of the axis of symmetry of the mirror 160. Light scattered by the particle is focused by the highly-reflective ellipsoidal mirror 160 to a spot at the second focal point of the mirror 160, and then passes onto the multielement detector 190.

In embodiments in which an ICCD detector is used for the mulitielement detector 190, the ICCD is gated to be open only when probe laser 150 fires. In some embodiments a small beam stop 220 may be placed in the path of the probe laser 150 to block the laser beam from the detector 190. In addition, in some embodiments, a spatial filter 170 may be placed at the second focal point of the mirror to help block stray light from reaching the detector 190.

The scattering cell geometry allows for scattered light to be sensed over nearly the entire backward scattering hemisphere with good resolution. In the embodiments using the ICCD multielement detector 190, a chip with 512×512 pixels provides for angular resolution of better than 0.35 deg over nearly the entire hemisphere. To make quantitative angular scattering measurements, a transformation is used to map the image on the mulitielement detector 190 (pixels x, y) to the particle scattering polar angle theta and azimuthal angle phi. In some embodiments scattered light from the particle is collected from angles subtending nearly the entire hemisphere in the backward scattering direction (polar angles theta from about 48 deg through 164 deg; and through all azimuthal angles phi ranging from 0 deg through 360 deg), covering approximately 63% of the 4 π steradian solid angle).

To determine the quantitative angular scattering measurements from a detection on the detector 190 we start with a point (x, y) on the detector 190 and want to determine what the value for $(\theta, \phi)$ for a ray that struck this point. The detector 190 has been centered so that x=0, y=0 is calibrated to be the on the optic axis (z). Also, this transformation procedure is for the angle theta range of $\pi/2$ to $\pi$.

$\phi$ is given by the equation: $\phi=\pi+\arctan(y/x)$, where the $\pi$ comes from the ray crossing the optic axis at the second focus point. To determine $\theta$, we note that all scattered rays originating at the first focus point of the ellipsoidal mirror will propagate through the second focus point of the mirror. These rays can be denoted with a second set of spherical coordinates $(\theta_2, \phi_2)$, where $\phi_2=\arctan(y/x)$, and $\theta_2=\arctan((y^2+x^2)^{(1/2)}/d)$, and where d is the distance from the second focus point to the detector 190.

For convenience, let $r^2=y^2+x^2$, so that $\theta_2=\arctan(r/d)$. Now each ray exiting the second focus point can be traced back to a reflection point on the ellipsoidal mirror with coordinates (x', y', z').

This second set of Cartesian coordinates is aligned with the center of the ellipsoidal mirror 160. Again, for simplicity, r' is used instead of x' and y'. The relationship between (r', z') and $(\theta_2, \phi_2)$ is given by $r'/(f-z')=\tan(\theta_2)$ where f is the distance from (x'=0, y'=0, z'=0) to the first focal point.

In addition, $(z'/a)^2+(r'/b)^2=1$ is the definition of an ellipsoid. With this equation, we can solve for r' and z' as follows: $r'=b\ \tan(\theta_2)*(bf+a(4b^2+(4a^2-f^2)\tan(\theta_2)^2)^{1/2})/(2(b^2+a^2*\tan(\theta_2)^2))$ and $z'=-(a^2(1-(r'/b)^2))^{1/2}$.

Finally, to calculate $\theta$ the following equation can be used: $\theta=\pi+\arctan(r'/z')$, where $\arctan(r'/z')$ is negative since z' is negative and will range from 0 to $-\pi/2$, thus $\theta$ will range from $\pi/2$ to $\pi$, as stated earlier.

Thus, via this process, scattering angles $(\theta, \phi)$ can be determined from detector 190 coordinates (x, y) and in embodiments with a ICCD multielement detector 190 from a pixel (x, y) location. We note that the coordinate transformation is non-linear. The ellipsoidal reflector compresses the angular scattering in some regions, and expands it in others.

Figure 3:
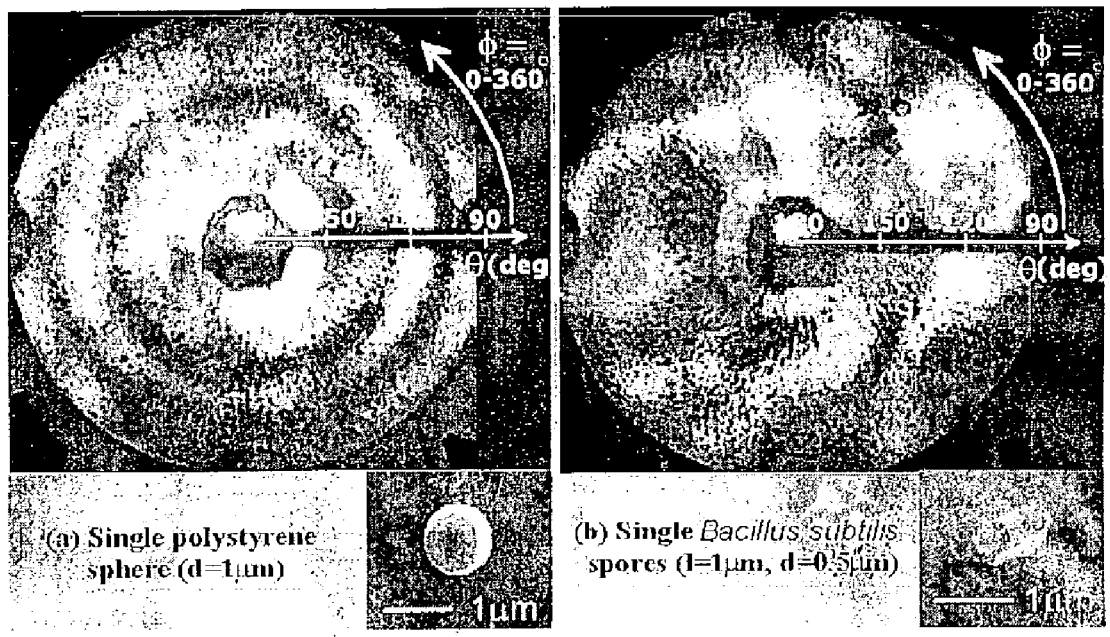

An example of two-dimensional scattering patterns obtained with the apparatus 100 is shown in FIG. 3. The pattern for a 1 micrometer diameter polystyrene latex sphere (a) shows the well-known ring structure expected by Mie scattering theory. By contrast, the pattern from a single non-spherical *Bacillus subtilis* (BG) spore (b) is far less symmetrical and has island-like features. Scanning electron images of the spheres are also shown for reference. The scattering patterns from different individual BG spores are not identical to each other because (1) the different BG spores, carried by the gas flow, are at random orientations related to the illuminating beam; and (2) the surface irregularity of BG spores varies from one to another, but all patterns are composed of intensity islands with similar sizes and shapes.

Figure 4:
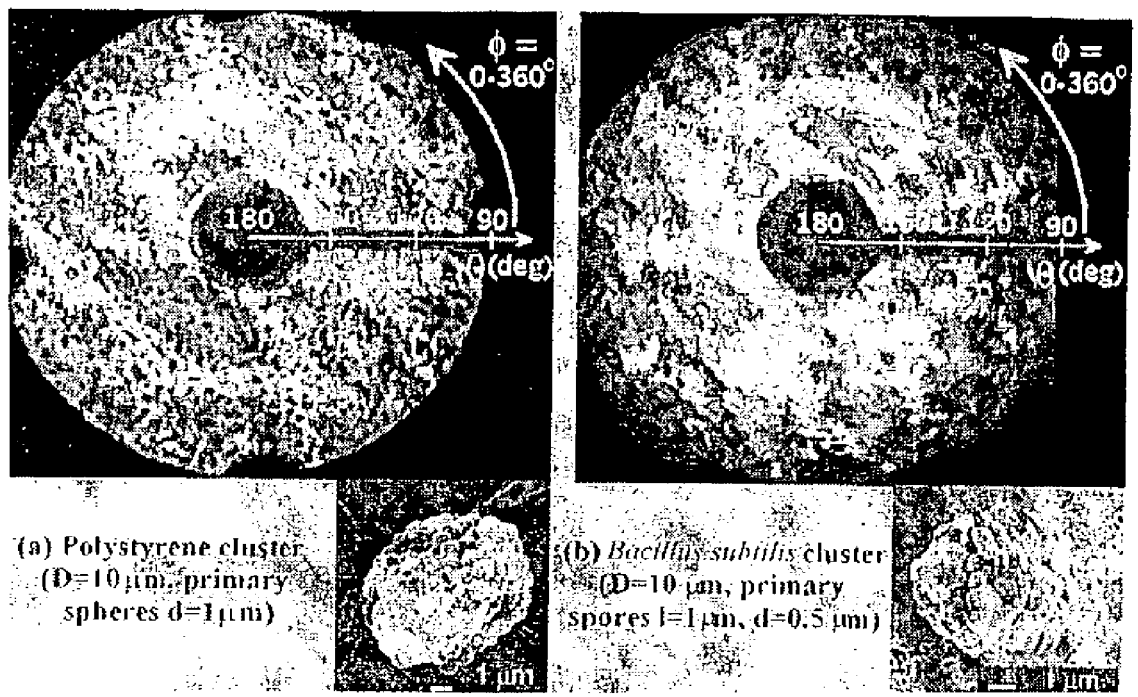

An example of two-dimensional scattering patterns obtained with the apparatus for aggregate clusters is shown in FIG. 4. Illustration (a) of FIG. 4 reveals the scattering pattern for a 10 micrometer size cluster of 1 micrometer diameter polystyrene latex spheres; whereas (b) shows the pattern for similar size clusters of BG spores. Scanning electron images of the clusters are also shown for reference. The two patterns of clusters formed by PSL-spheres and BG-spores can be readily distinguished. These patterns suggest that, using fast computer image processing, suspect potentially harmful aerosols can be detected, in-situ and in real time, by their characteristic scattering patterns and differentiated from background aerosols. In an alternate embodiment of the apparatus 100, by placing a mirror at the beam stop 220, and adjusting the probe laser 150 beam alignment so that only the reflected beam intersects the particle stream, the probe laser 150 beam direction can be reversed, providing for scattered light to be sensed over nearly the entire forward scattering hemisphere, rather than the backward hemisphere.

In another alternate embodiment of the apparatus 100, the probe laser 150 may be directed to enter the ellipsoidal mirror 160 in a direction perpendicular to the axis of the ellipsoidal mirror 160, but still through the same focal point of the mirror 160. With this arrangement, scattering for polar angles near 0 deg through near 180 deg, and azimuthal angles that subtend 180 deg, is measured (the limits of scattering detected in the forward and backscatter directions is determined by the size of the probe laser 150 inlet and outlet ports in the mirror 160).

The present invention provides one of more of the following distinct advancements over previous art: 1) the design uses (the relatively expensive) probe laser 150 energy very efficiently. To excite scattering by single particles with a small amount of laser energy, a highly focused, pulsed laser is used. The laser is triggered to fire only when a particle is within the sample volume. Thus, laser energy is conserved and only expended during the small fraction of time when a particle is being sampled. Further, the probe laser is highly focused (and consequently has high intensity) in a tiny spatial region that includes the particle of interest, thereby reducing the contribution of unwanted molecular Rayleigh scattering by the gaseous medium in which particles are entrained. 2) A gated detector is used. Scattered light is only detected for a few tens of nanoseconds overlapping the period when the probe laser fires, reducing the contribution of stray light to the scattering signal, and contributing to a good signal-to-noise ratio throughout the TAOS image. 3) A relatively large angular region of particle scattering is sensed with high angular resolution. A nearly 2 π steradian solid angle of scattering is sensed in the backward (or forward, or side) scattering hemisphere, and angular resolution can be better than 1 deg (depending on the number of pixels in the ICCD chip in the exemplar). 4) ICCD or other detectors 190 with relatively uniform quantum efficiency for all pixels can be employed in the invention, providing more quantitative angular scattering measurements than can be obtained with multiple photodiode or multi-anode photomultiplier tube detectors. 5) In some embodiments, even though the sample volume is small (of the order of 100 micrometer across), the exploitation of an aerosol virtual impactor concentrator and aerodynamically focusing nozzle provides for practical sample rates for atmospheric aerosols, at least for supermicrometer-sized particles. Sample rate is of the order of 10 liters per minute. However, with the virtual impactor/aerodynamic focusing nozzle inlet, the sample rate is particle size-dependent and must be measured to allow for quantitative measurements.

Probe lasers 150 may be designed using one or more lasers at different wavelengths, as noted above. For two laser wavelengths, the multielement detector 190 can be masked by two interference filters (not shown in FIG. 1) highly transmittive at the two wavelengths, each covering half of the pixels, thereby allowing for detection of ½ of a hemisphere scattering at one wavelength and a complementary ½ hemisphere scattering at the other wavelength.

In an alternative embodiment of this technique, angular scattering may be obtained at both laser wavelengths over a larger angular region by using a fiber optic bundle to collect scattering from different spatial regions, and the multielement detector 190 could be divided into many rectangular regions, with alternating regions passing one wavelength, the other passing the other wavelength.

In another embodiment of this technique, the two (different wavelength) pulsed lasers can be triggered to fire at slightly different times, and two synchronized multielement detectors 190 (only one shown in FIG. 1) may be used for detection, one gated to be open during the period of the first laser firing, and the other to be gated to be open during the period of the second laser firing. In this way, one multielement detector 190 senses the angular scattering pattern at one wavelength and the second multielement detector senses the angular pattern at the other wavelength, without the need for interference filters.

In another embodiment of this technique, for application to the infrared (2–12 micrometer) wavelength region, one or more InSb or HgCdTe cameras can be used as the multielement detector(s) 190. The ellipsoidal mirror 160 can be coated to be highly reflective within the particular wavelength region of interest. For the two infrared laser wavelengths, one multielement detector 190 can be masked by two interference filters, highly transmittive at the two wavelengths, each covering half of the pixels, thereby allowing for detection of ½ of a hemispheric scattering at one wavelength and a complementary ½ hemispheric scattering at the other wavelength.

Figure 2:
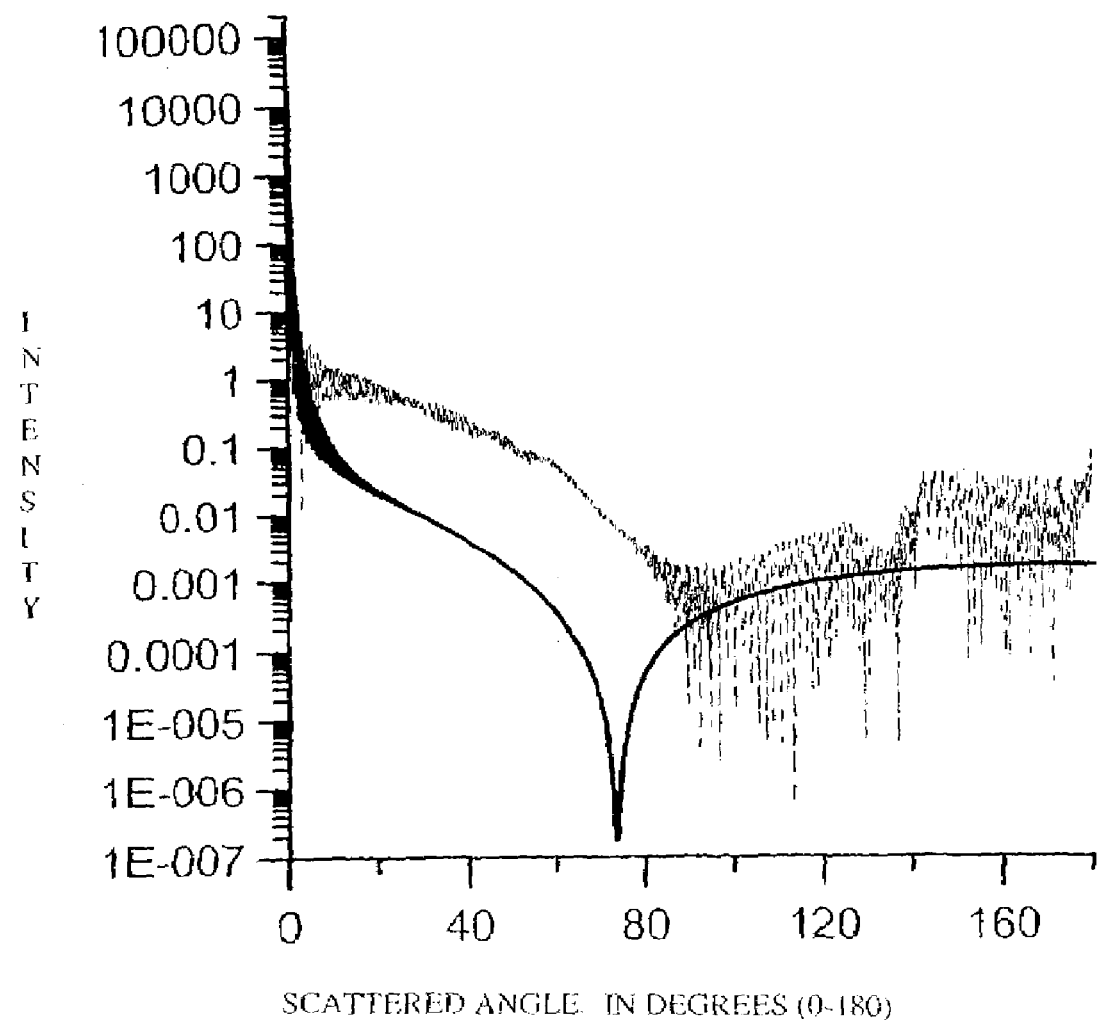

To illustrate the method of the invention for determination of particle absorption characteristics in a simple case, consider a homogeneous spherical water droplet that might contain a small quantity of dissolved absorbing material. FIG. 2 illustrates the basic methodology. Shown is the calculated one-dimensional polar angular scattering from two different water droplets illuminated with 266 nm light. The horizontal axis represents scattering angle from 0 to 200 degrees. The vertical axis represents relative intensity of scattered light, where a level of 1 represents average scattered light in all directions from a particle. The pure water droplet (illustrated by the dashed line) is non-absorbing, while the doped water droplet (illustrated by a solid line) contains one percent tryptophan, which absorbs strongly at a wavelength of 266 nm. At polar angles between 15 and 80 degrees the scattering for the absorbing droplet is 30 to 100 times smaller than by the non-absorbing droplet. The decreased scattering of the absorbing particle depends upon the size of the sphere.

The absorption in this case is small and consequently is approximately proportional to the imaginary part of the refractive index ($m_i$). The term "refractive index" is used to refer to the real part of the refractive index ($m_r$). The complex refractive index is $m=m_r+i\, m_i$ where i is the square root of 1. Both $m_r$ and $m_i$ are wavelength dependent. For the first droplet with no tryptophan, the absorption index $m_i=0$. For the second droplet with 1% tryptophan, the $m_i=0.012$. Thus, the presence of tryptophan (or other absorbing material) and the approximate absorption index can be determined.

If the particles or droplets are known to be spherical, homogeneous, isotropic, and to have known real refractive index $m_r$, and if only the absorption at one wavelength is desired, then a single-wavelength angular measurement should be adequate to determine the absorption. If the real refractive index is not known then the inversion to obtain the absorption index is easier if a second wavelength is used.

However, if the particle may be non-spherical, then it is important to have the angular distribution at wavelengths that are not absorbed as well as at the wavelengths where there is absorption.

Two cases are mentioned, differing in the numbers of wavelengths used and the amount of information that can be obtained. A single wavelength, chosen to be on an absorption line, may be used if the particles are spherical and $m_r$ is known. Then the scattering can be calculated for different $m_i$ and stored in lookup tables, and/or specific cases can be calculated as needed. The instrument is also calibrated with particles of known $m_r$ and $m_i$ so that the measured angular scattering can be compared with the calculated angular scattering. Then for any unknown particle a computer program can be written to do a search (e.g., least squares minimization using a gradient search routine (see, e.g., the book Numerical Recipes, $2^{nd}$ ed., by W. H. Press et al., (Cambridge, 1992) to determine the particle's absorption using one-dimensional angular scattering. Because the intensities have such a large variation with angle, the cost function to be minimized is the sum over angles of $(I_c-I_m)/I_{avg}$, where $I_c$ is the calculated intensity at that angle, $I_m$ is the measured intensity at that angle, and $I_{avg}$ is the average intensity over an angular range of a few (e.g., 5) degrees centered around that angle. If $m_r$ is not known, then a two-dimensional gradient search is required within the range of uncertainty in $m_r$ and $m_i$. If the particle is nonspherical, then depending upon its orientation at the time it is measured, different results for $m_i$ will be obtained. If the nonsphericity is small, (e.g., 5 percent), the error in the $m_i$ will also be small. However, for highly nonspherical particles, the errors may be large. If the particles are ellipsoidal or spheroidal, then the measured and calculated two-dimensional angular scattering (TAOS) patterns can be compared: gradient search techniques can be used to minimize the squared difference between these measured and computed TAOS. With the capabilities of presently available computers such comparisons to find the parameters ($m_r$, $m_i$, size and one (spheroids), or two (ellipsoids) parameters indicating shape) that give the best fit between measured and computed TAOS would be highly time consuming unless the nonsphericities and initial uncertainty in $m_r$ were small. If the particles of interest can be described by a small number of parameters, e.g., ratio of axes in spheroids, or the number N (where N is not too large, e.g., less than 20) of known-diameter primary spheres that make up an aggregate particle, then this technique of calculating the TAOS and searching for the parameters that minimize the squared differences will work, and as computer capabilities increase, should work for more and more complex particles. However, for arbitrary particles, e.g., particles which may be aggregates of particles of different compositions, sizes, and shapes, there would be too many parameters to compute, and too many particles having similar scattering functions, to unambiguously determine the detailed composition and structure.

If two wavelengths are used, one wavelength may be chosen to be on an absorption band of interest, and the other off the absorption band. Two-dimensional (polar and azimuthal) angular scattering measurements are required if the particles are not spherical. If the two wavelengths are close to each other and are both on an absorption band (or both off an absorption band), the scattering patterns will be essentially the same. However, if only one wavelength is in the absorption band and the other nearby wavelength is in the transparent band, then even if the two wavelengths are close to each other, the angular scattering patterns will be different if the particle is significantly absorbing ($m_i$ is not too small). The methods described above for comparing the measured and computed TAOS patterns can be used, but will be find the results quicker and/or with less uncertainty because the additional information from both TAOS patterns will be included in the cost function to be minimized.

In an alternate set of embodiments, the thermal emission from the particle is measured and used (in most embodiments with a second scattering measurement) to determine the absorption by the particle. When a particle absorbs light the temperature of the particle increases, the thermal emission increases, and the thermal emission shifts to shorter wavelengths. The probe laser 150 that emits light at the wavelength at which the absorption is to be determined, is termed the first probe laser 150. Except in special cases where sufficient prior information is known about the particles, a second probe laser 150 will be required to help determine the absorption from the measured signals. This second probe laser will be at a wavelength that absorbs only little or negligible light. This second probe laser 150 will in most embodiments be in the visible range. The probe lasers may be collinear (being combined with, e.g., a beam splitter or dichroic mirror), but need not be. In some embodiments, only one element of the multielement detector 190 may be sufficient to determine the elastic scattering from this second probe laser. To measure the thermal emission, the instrument in FIG. 1 can be used if the multielement detector 190 is set to the appropriate range for thermal emission, typically in the 2 to 14 micrometer range (the trigger lasers 270 and 271 and trigger detectors 140 and 141 need not change). In the case of thermal emission, the spectral composition of the emission is more useful for determining absorption than is the angular distribution. The multielement detector 190 will, in one embodiment, be composed of detectors that are sensitive to different wavelength bands (such wavelength sensitivity can be achieved using different bandpass or cutoff filters and/or different materials, e.g., InSb and HgCdTe). In another embodiment, a grating or other dispersing element (possibly along with slits and mirrors as necessary) will be used to disperse the thermal emission before it reaches the multielement detector 190. The first probe laser 150 need not be pulsed (as was emphasized above); the decision to use a pulsed or continuous wavelength laser will be made depending up the available sources at each wavelength at which the absorption is to be measured. The wavelength of the probe laser will be out of the range of sensitivity of the multielement detector 190. For example, if the wavelength of the first probe laser 190 is 5 um, the multielement detector 190 should either have a band-blocking filter at 5 um placed in front of it, or consist of elements that are not sensitive to 5 um (e.g., this multielement detector in one embodiment may be sensitive from 3 to 4.5 um and from 5.5 to 14 um). The instrument is calibrated with particles of known size and absorption. For any unknown particle the absorption is determined (by the computer) using a lookup table with interpolation, based on the scattering signals at both absorbing and non-absorbing wavelengths.

In the present invention, unlike the florescence technique, the intensity of scattered light is measured through a relatively large (approximately $2\pi$ steradians solid angle) angular range. From the angular distribution of scatter light, particle absorption and morphology can be inferred, or at least bounded.

One advantage of absorption measurements over fluorescence is that absorption can provide much more information about particles. IR absorption of pure compounds can be like a fingerprint of that compound, whereas fluorescence is less specific. In addition, most materials do not fluoresce strongly enough for them to be detected as single particle fluorescence in an air sampler.

The advantage of absorption measurements over Raman emission is that absorption can cause changes in scattering signals that are relatively easy to detect, while Raman emission is relatively weak. Even with a very powerful laser source it would be impossible to measure single-shot single-particle Raman spectra with any significant spectral resolution. To date no capability for single-particle, single-shot measurements of spectrally dispersed, or even un-dispersed, Raman emission has been demonstrated.

There are methods for measuring Raman from particles that have been collected on surfaces, but these cannot be real-time methods; further, the particles may change on impact or after collection.

There are aerosol measurement challenges to which this present invention may be useful. Detection of small numbers of airborne biological warfare agents mixed with an innocuous background is one of special interest. The present invention may also be applied to detection of airborne particles such as pollutants, allergens, biological warfare agents, toxins, pollens, bacteria, infectious agents (e.g., in hospitals), particles used in or affecting manufacturing processes or agriculture.

While the preferred embodiment and various alternative embodiments of the invention have been disclosed and described in detail herein, it may be apparent to those skilled in the art that various changes in form and detail may be made therein without departing from the spirit and scope thereof.

We claim:

1. An apparatus for determining absorption and shape characteristics of individual airborne particles comprising:
   an aerosol concentrator to draw air containing particles of interest and deliver a significant fraction of the desired particles in an outlet flow to a nozzle;
   a nozzle, coupled to said aerosol concentrator, producing an aerodynamically focused aerosol jet, thereby providing a second stage of aerosol concentration, in a particle sample volume;
   a first trigger laser emitting a beam of wavelength $\lambda_1$ and focused in a trigger region through which particles flow on their way to a detection region;
   a second trigger laser emitting a beam of wavelength $\lambda_2$ aimed in a direction approximately orthogonal to the direction of the first trigger laser and focused in the trigger region, the trigger region being defined by the intersection of the beams of the first and second trigger lasers;

a first wavelength-selective photodetector sensitive to light scattered from the individual airborne particles in the trigger region and emitting a first output signal in response to light of wavelength $\lambda_1$;

a second wavelength-selective photodetector sensitive to light scattered from particles in the trigger region and emitting a second output signal in response to light of wavelength $\lambda_2$;

at least one probe laser configured to emit a pulse of light focused on the particle sample volume, the particle sample volume being slightly downstream of the trigger volume, and triggered by the logically ANDed first and second output signals of the first and second wavelength-selective photodetectors, to emit the pulse of light;

an ellipsoidal mirror, having a first and second focal plane, where the particle sample volume substantially coincides with the first focal plane, where the ellipsoidal mirror is deployed to collect and focus the light scattered by individual airborne particles;

a multi-element detector for measuring the spatial distribution of light scattered by individual airborne particles;

a spatial filter placed at the second focal point of the ellipsoidal mirror to block stray light from entering the multi-element detector;

a means for transforming the measured spatial distribution of light scattered by individual airborne particles into an angular scattering of light scattered from the individual airborne particles; and a means of determining characteristics of light absorption and morphology of the individual airborne particles from the angular scattering of light.

2. The apparatus for determining absorption and shape characteristics of individual airborne particles of claim 1 further comprising an eduction tube for evacuating the second stage of aerosol concentration.

3. The apparatus for determining absorption and shape characteristics of individual airborne particles of claim 1 wherein said probe laser enters the ellipsoidal mirror through a port on the axis of symmetry of the ellipsoidal mirror.

4. The apparatus for determining absorption and shape characteristics of individual airborne particles of claim 1, wherein said probe laser enters the ellipsoidal mirror through a port perpendicular to the axis of symmetry of the ellipsoidal minor.

5. The apparatus for determining absorption and shape characteristics of individual airborne particles of claim 1, wherein said multi-element detector is also triggered by the logically ANDed outputs of the first and second wavelength-selective photodetectors.

6. The apparatus of claim 1, wherein said multi-element detector further comprises an ICCD detector array.

7. The apparatus of claim 1, wherein said multi-element detector further comprises a CCD detector array.

8. The apparatus of claim 1. wherein said multi-element detector further comprises a multiple-anode photomultiplier tube detector.

9. The apparatus of claim 1, wherein at least one probe laser emits light in the ultraviolet range.

10. The apparatus of claim 1, wherein said aerosol concentrator further comprises a virtual impactor concentrator.

11. The apparatus of claim 1, further comprising:

an airtight box encompassing the ellipsoidal mirror, the first trigger laser, the second trigger laser, the first wavelength-selective photodetector, the second wavelength-selective photodetector, at least one probe laser, and the multi-element detector;

a means for evacuating air from the airtight box; and a means, coupled to the air evacuation means, for measuring and controlling flow of evacuated air from the airtight box; and wherein said nozzle is mounted to an inlet of the airtight box for concentrating particles into a thin jet of focused, laminar flow, particle laden, air such that the individual airborne particles may be probed with the probe laser at practical sample rates.

12. The apparatus of claim 1, wherein said means of determining characteristics of light absorption and shape of the particle from the angular scattering of light further comprise a means for comparing a measured and calculated two-dimensional angular scattering patterns (TAOS) using a gradient search technique to minimize the squared difference between these measured and computed TAOS.

13. An apparatus for determining the light absorption of individual airborne particles comprising:

an aerosol concentrator to draw air containing particles of interest and deliver a significant fraction of the desired particles in an outlet flow to a nozzle;

a nozzle, coupled to said aerosol concentrator, producing an aerodynamically focused aerosol jet, thereby providing a second stage of aerosol concentration, in a particle sample volume;

a first trigger laser emitting a beam of wavelength $\lambda_1$ and focused in a trigger region through which particles flow on their way to a detection region;

a second trigger laser emitting a beam of wavelength $\lambda_2$ aimed in a direction approximately orthogonal to the direction of the first trigger laser and focused in the trigger region, the trigger region being defined by the intersection of the beams of the first and second trigger lasers;

a first wavelength-selective photodetector sensitive to light scattered from the individual airborne particles in the trigger region and emitting a first output signal in response to light of wavelength $\lambda_1$;

a second wavelength-selective photodetector sensitive to light scattered from particles in the trigger region and emitting a second output signal in response to light of wavelength $\lambda_2$;

at least one probe laser configured to emit a pulse of light focused on the particle sample volume, the particle sample volume being slightly downstream of the trigger volume, and triggered by the logically ANDed first and second output signals of the first and second wavelength-selective photodetectors, to emit the pulse of light;

an ellipsoidal mirror, having a first and second focal plane, where the particle sample volume substantially coincides with the first focal plane, where the ellipsoidal mirror is deployed to collect and focus the light scattered by individual airborne particles;

a multi-element detector for measuring the spatial distribution of light scattered by individual airborne particles;

a spatial filter placed at the second focal point of the ellipsoidal mirror to block stray light from entering the multi-element detector;

a means for transforming the measured spatial distribution of light scattered by individual airborne particles into an angular scattering of light scattered from the particle;

a means of determining characteristics of light absorption and morphology of the individual airborne particles from the angular scattering of light; and a means for determining light absorbed by the individual airborne particles from characteristics of light absorption and morphology of the individual airborne particles.

14. The apparatus of claim 13, further comprising:

an airtight box encompassing the ellipsoidal mirror, the first trigger laser, the second trigger laser, the first wavelength-selective photodetector, the second wavelength-selective photodetector, at least one probe laser, and the multi-element detector;

a means for evacuating air from the airtight box; and a means, coupled to the air evacuation means, for measuring and controlling flow of evacuated air from the airtight box; and wherein said nozzle is mounted to an inlet of the airtight box for concentrating particles into a thin jet of focused, laminar flow, particle laden, air such that the individual airborne particles may be probed with the probe laser at practical sample rates.

15. The apparatus of claim 13, wherein said means for determining light absorbed by the individual airborne particles further comprises a means for comparing the measured and calculated two-dimensional angular scattering patterns (TAOS) using a gradient search technique to minimize the squared difference between these measured and computed TAOS.

16. A method of determining absorption by individual airborne particles flowing in a fluid aerosol jet, comprising the steps of:

producing, with a nozzle, a focused aerosol jet having a predetermined diameter;

defining a trigger volume in the fluid by intersecting a plurality of substantially orthogonally aimed trigger laser beams, each of a different wavelength;

detecting light scattered from the vicinity of the trigger volume by a plurality of particle detectors each sensitive to a wavelength corresponding to the wavelength of one of orthogonally aimed trigger laser beams;

probing the individual airborne particles with at least one probe laser triggered by the particle detectors, said probe laser producing a beam with a diameter approximately matching the diameter of the fluid aerosol jet such that the probe laser illuminates a region the focused aerosol jet;

measuring the angular structure of light scattered from the individual airborne particles in a detection volume;

determining the light characteristics absorbed by the particle from the measured angular structure of light scattered.

17. The method of claim 16, wherein the at least one of the particle detectors is sensitive to thermal emission at wavelengths in the 3 to 12 um range which do not overlap with the wavelength of the probe laser.

18. The method of claim 16, wherein said step of determining the light characteristics absorbed by the particle further comprises the step of comparing a measured and calculated two-dimensional angular scattering patterns (TAOS) using a gradient search technique to minimize the squared difference between these measured and computed TAOS.

* * * * *